(12) United States Patent
McGee et al.

(10) Patent No.: US 7,043,958 B2
(45) Date of Patent: May 16, 2006

(54) GAS ANALYZER AUTOMATED PURGE/ZERO PROCESS

(75) Inventors: Phillip McGee, Owatonna, MN (US); Robert Kochie, Mantorville, MN (US); Durval S. Ribeiro, Owatonna, MN (US); Manokar Chinnandurai, Owatonna, MN (US)

(73) Assignee: SPX Corporation, Charlotte, NC (US)

( * ) Notice: Subject to any disclaimer, the term of this patent is extended or adjusted under 35 U.S.C. 154(b) by 0 days.

(21) Appl. No.: 10/321,585

(22) Filed: Dec. 18, 2002

(65) Prior Publication Data

US 2004/0060341 A1 Apr. 1, 2004

Related U.S. Application Data

(60) Provisional application No. 60/413,738, filed on Sep. 27, 2002.

(51) Int. Cl.
*G01N 37/00* (2006.01)

(52) U.S. Cl. ...................... 73/1.07; 73/23.21

(58) Field of Classification Search .............. 73/1.07, 73/23.2, 23.21, 23.32, 1.34; 702/100
See application file for complete search history.

(56) References Cited

U.S. PATENT DOCUMENTS

| | | | | |
|---|---|---|---|---|
| 3,559,491 A | * | 2/1971 | Thoen | 73/863.24 |
| 3,924,442 A | * | 12/1975 | Kerho et al. | 73/23.21 |
| 4,151,738 A | * | 5/1979 | Hyer et al. | 73/23.21 |
| 4,555,930 A | * | 12/1985 | Leach et al. | 73/23.2 |
| 4,687,934 A | * | 8/1987 | Passaro et al. | 250/343 |
| 4,947,339 A | * | 8/1990 | Czekajewski et al. | 702/24 |
| 5,001,463 A | * | 3/1991 | Hamburger | 340/627 |
| 5,239,492 A | * | 8/1993 | Hartwig et al. | 73/1.07 |
| 5,597,535 A | * | 1/1997 | Schaedlich et al. | 73/1.07 |
| 5,610,398 A | * | 3/1997 | Anderson et al. | 250/339.12 |
| 5,993,743 A | | 11/1999 | Nordman et al. | |
| 6,675,629 B1 | * | 1/2004 | Aldridge et al. | 73/1.07 |
| 6,786,217 B1 | * | 9/2004 | Stenzler | 128/204.23 |
| 2003/0136176 A1 | * | 7/2003 | Ruiz | 73/23.2 |

OTHER PUBLICATIONS

"Gas-Sentry Detector Operation and Calibration Manual", Bascom-Turner Instruments, Aug. 1999.*

* cited by examiner

Primary Examiner—Michael Cygan
(74) Attorney, Agent, or Firm—Baker & Hostetler LLP

(57) ABSTRACT

An apparatus and method for purging and zeroing an analyzer. At times, for good analysis of a gas sample or taking a live reading, the analyzer needs to be zero out and/or purge of contaminants. The analyzer can take a live reading, purge and/or zero in any order. The purge function and zero function can automatically be done before, during or after taking a live reading.

20 Claims, 9 Drawing Sheets

GAS ANALYZER AUTOMATED PURGE/ZERO PROCESS

PRIORITY

This application claims benefit of U.S. provisional patent application Ser. No. 60/413,738, filed on Sep. 27, 2002, which is incorporated herein by reference.

FIELD OF THE INVENTION

Embodiments of the present invention generally relate to an analyzer. More specifically, a gas analyzer having an automatic purge/zero process.

BACKGROUND OF THE INVENTION

Gas powered vehicles produce emissions of various gases leading to pollution of the air. Most states require yearly vehicle inspection as part of the privilege of driving in their states. However, some states, such as California, have required stricter emission standards for the vehicles of their citizens. Thus, testing facilities and repair garages are performing more tests as the regulations become tighter.

In the past, only hydrocarbons (HC) and carbon monoxide (CO) had to be measured during inspection, but stricter regulations require the measurement of oxygen ($O_2$), carbon dioxides ($CO_2$) and nitrous oxides (NOx), as well. The vehicle must pass inspection, including emissions testing, in order to obtain a valid inspection sticker. If the vehicle fails the inspection, then it must be repaired before it will pass inspection. In the repair process, a mechanic must be able to determine if the repair of the gas emission system was successful.

Gas analyzers have been developed in order to help the mechanic diagnose the emission problems. Large platform analyzers were originally developed to measure the emission gases and were moved around on carts. However, large platform analyzers are too large for small garages to operate and store. Additionally, the large platform analyzers are typically very expensive for a small repair garage to own.

"Portable" gas analyzers were subsequently developed for use to analyze emissions. While the portable gas analyzers were smaller, they still weighed between twenty–thirty pounds and are too large to be held in the operator's hands. Because the portable analyzers were still big, they required a big pump to circulate the emission gases throughout the analyzer for measuring. Additionally, a large and heavy filtering device to filter the particulate and moisture from the emission gases. The big pump also required a large power source, thus increasing the weight of the portable gas analyzer. The portable gas analyzer has a large chassis to hold the various components together. The large size of the chassis increased the weight of the analyzer.

As the analyzer operates, emission gases including condensation from the line (due to a hot emission source traveling in hoses that are at ambient temperature) are filtered through the filter. However, the analyzer can have many filters that each requires individual hoses so that additional contamination (contamination from the inside of the hose) and condensation (more hoses leads to more condensation) can occur leading to false readings.

In order to circulate the emission gases, a pump is utilized. However, the pump can be big because of the size of the analyzer. The pump is solidly mounted onto a chassis located near the bottom of the analyzer. Additionally, the pump vibrates during operation, thereby, transmitting the vibration to the operator, and making it uncomfortable for the operator to use the analyzer.

Therefore, there is a need for an analyzer that can be lightweight, compact, and portable. There is also a need for an integrated multistage filter system to reduce contamination and condensation. Another need includes an analyzer that can notify the operator that it is in the wrong orientation for a purging operation so that more liquids can be purged. A further need includes an analyzer with reduce vibration from the pump so that the analyzer is more comfortable to use. There is still a further need for an analyzer that can purge and recalibrate ("zero out") as needed.

SUMMARY OF THE INVENTION

Embodiments of the present invention generally provide for an analyzer that is portable, lightweight and compact and includes a multistage filter. The analyzer can have an orientation component, can have less vibration, and can purge and/or zero manually or automatically.

In one embodiment of the invention, an analyzer is provided and can include a sensor function that can take readings of a sample of gas supplied from an inlet, a zero function that can reset said sensor to a baseline, and a purge function that can purge the analyzer of a contaminant, wherein the sensor function, the zero function and the purge function can be in communication with each other. When said sensor function is actuated, the zero function and the purge function can be automatically actuated. When said sensor function is actuated, the zero function and the purge function can be simultaneously actuated with each other. When said sensor function is actuated, the zero function can be automatically actuated followed by the purge function. When said sensor function is actuated, the purge function may be automatically actuated followed by the zero function. When said sensor function is actuated, the zero function and the purge function may be simultaneously and automatically actuated. The purge function can occur before at least one of zero function and sensor function. The zero function may occur before at least one of purge function and sensor function. The sensor function may occur before at least one of zero function and purge function.

In another embodiment, a method of actuating is provided and may include a sensor function of the analyzer to take a reading of a sample of gas supplied by an inlet, actuating a zero function of the analyzer to zero out the analyzer, and actuating a purge function of the analyzer to purge a contaminant from the analyzer. Actuating the sensor function automatically can actuate the zero function and the purge function. Actuating the sensor function, can automatically actuate the zero function followed by the purge function. Actuating the sensor function, can automatically actuate the purge function followed by the zero function. Actuating the sensor function can actuate the zero function and the purge function simultaneously and automatically. Actuating the purge function can occur before at least one of actuating the zero function and actuating the sensor function. Actuating the zero function can occur before at least one of actuating the purge function and actuating the sensor function. Actuating the sensor function may occur before at least one of actuating the purge function and actuating zero function.

In still another embodiment, a system for operating an analyzer can include a means for taking live reading of a gas sample, a means for purging a contaminant from the analyzer, and a means for zeroing a sensor of the analyzer, wherein the means for taking live reading, the means for purging and the means for zeroing may be in communication with each other. The means for purging may occur before at least one of means for zeroing and means for taking live reading. The means for purging may occur before at least one of means for zeroing and means for taking live reading. The means for taking live reading may occur before at least one of means for zeroing and means for purging. When the means for taking live reading is actuated, the means for purging and the means for zeroing may be automatically actuated.

There has thus been outlined, rather broadly, the more important features of the invention in order that the detailed description thereof that follows may be better understood, and in order that the present contribution to the art may be better appreciated. There are, of course, additional features of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE PREFERRED EMBODIMENT

The embodiments of the present invention relate to a portable analyzer that is portable, lightweight, and compact. The analyzer is constructed and arranged so that smaller, lightweight components can be selected and that the components are made from lightweight materials. The analyzer can have an orientation device that determines its orientation so that efficient purging of contaminants and liquids are conducted. An efficient, compact integrated filter is also provided to filter contaminants and liquids, such as water, from the emission gases. Additionally, embodiments of the present invention include reducing the vibration of components of the analyzer during operation, such as the pump, and to purge and zero out the analyzer as needed.

Figure 1:
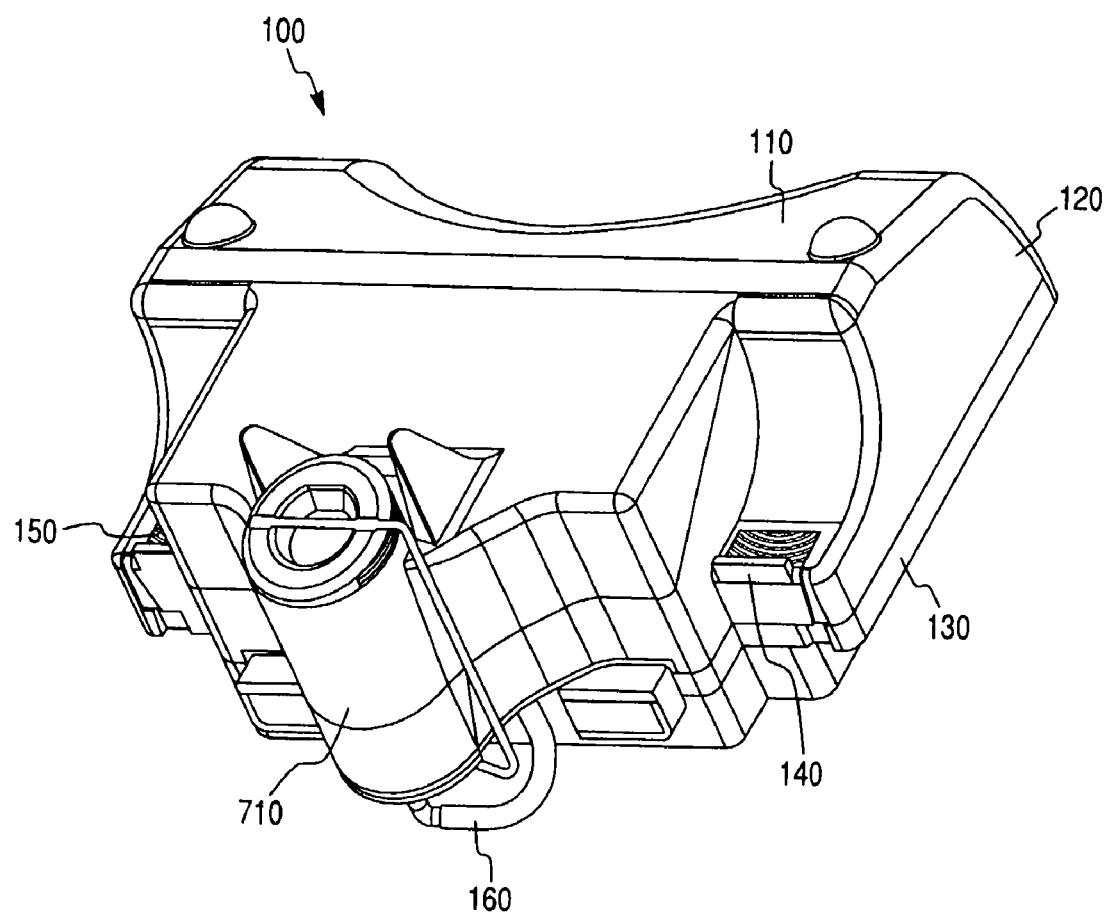
FIG. 1 is a perspective view of a portable analyzer according to an embodiment of the invention.

FIG. 1 is a perspective view of a portable analyzer 100 according to an embodiment of the invention. The analyzer 100 includes a housing 110 having an upper portion 120 and a lower portion 130. Moveable latches 140 are provided in the upper portion 120 to couple to another device, such as the Genisys™ (from Service Solutions, Owatonna, Minn.). The latches 140 include grooves 150 on an upper surface and can be easily coupled or uncoupled with another device. A filter 710 (greater detail in FIG. 7) is provided having an inlet hose 160 that can receive gases, such as emission gases from a vehicle, and an outlet to exhaust the gases after analysis and to exhaust contaminates, including water.

In one embodiment of the invention, the portable analyzer 100 is lightweight and small enough to be comfortable in a hand(s) of the operator. Preferably the analyzer 100 weighs about 2 pounds or less and has dimensions of about 6.4 inches (length) by 4.9 inches (height) by 3.9 inches (depth). The analyzer 100 can weigh less because the housing 110 is preferably made from a lightweight polymer that is resistant to particles, such as dusts, from accumulating on the surface. The polymer can be acrylonitrile butadiene styrene (ABS) plastic. ABS is a strong, high-density plastic that is resistant to particles sticking to its surfaces, hence, contamination and the weight of the analyzer are decreased.

With the use of a smaller manifold (FIG. 2), the various components of the analyzer 100 will have to be smaller and thus lighter. Because the components can be smaller and lighter, the analyzer weighs less and is smaller in dimensions. Due to the analyzer 100 being lighter and smaller than conventional analyzers, more can be on hand in smaller garages because it takes less storage space. Because of the reduced weight and dimensions, the analyzer 100 is cheaper to ship, which saves money for consumers, and can be held by the operator for a longer period of time then a heavier analyzer.

Figure 2:
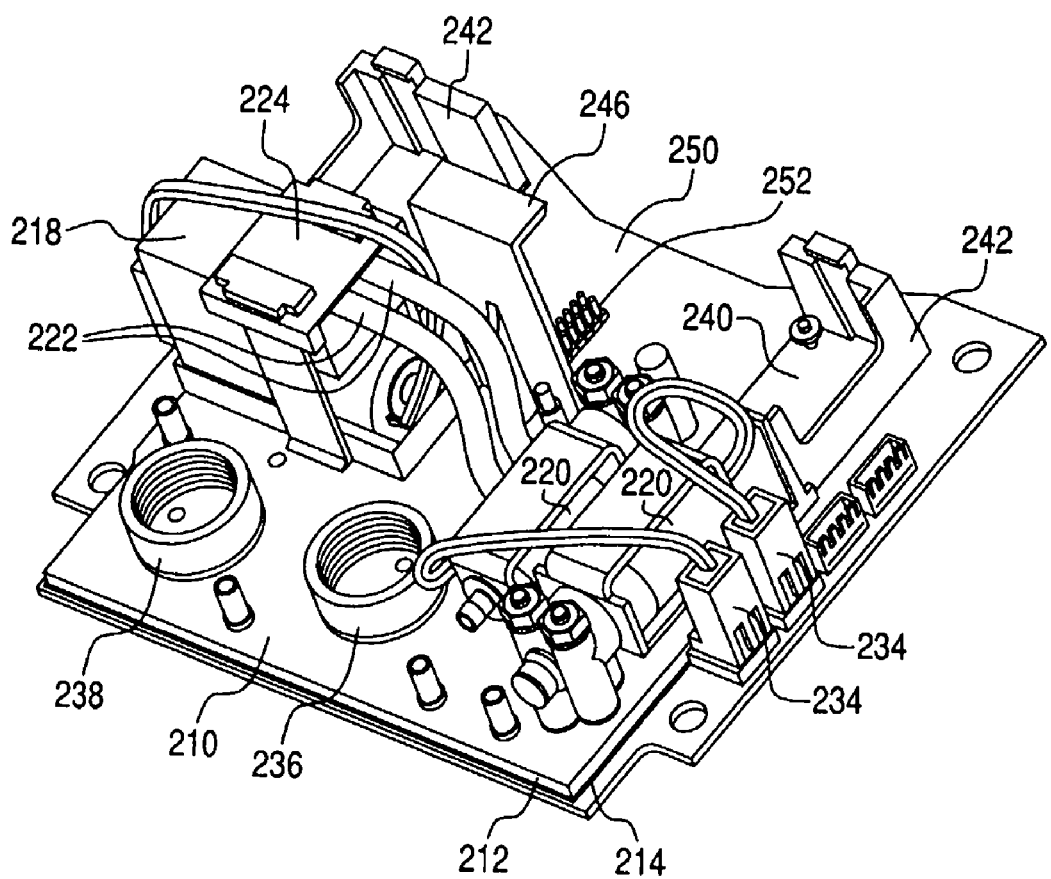
FIG. 2 is a perspective view of an embodiment of a manifold with components thereon.

FIG. 2 is a perspective view of an embodiment of a manifold 210 with components thereon. The upper and lower portions 120 and 130 have been removed to illustrate an embodiment of the manifold 210 of the present invention. Conventional analyzers have a chassis coupled to the manifold 210 thereby, making it heavier. In one embodiment, the chassis is removed and is no longer coupled to the manifold 210 in order to decrease the weight of the analyzer 100. The manifold 210 is smaller than conventional manifolds and includes gas passages therein to allow gases to travel throughout the analyzer 100 until it is exhausted out. Manifold 210 can be made from a strong lightweight material, such as ABS. Because the manifold 210 is made from ABS and is smaller than conventional manifolds, the analyzer 100 is lighter and smaller in dimensions.

Figure 4:
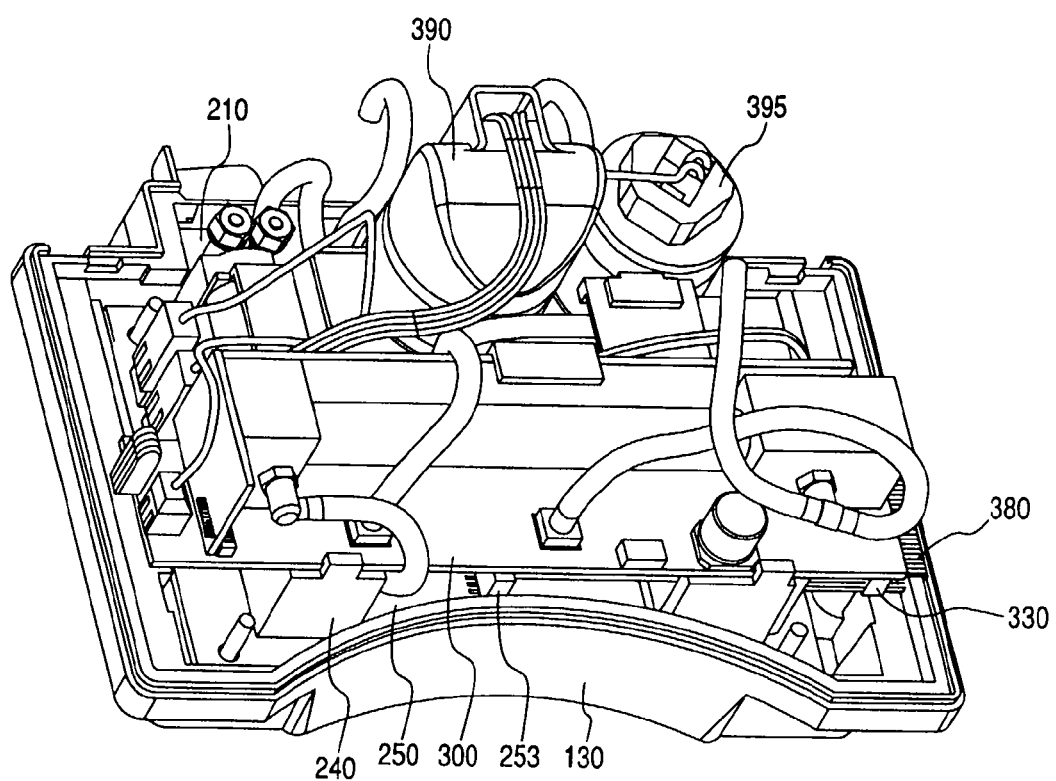
FIG. 4 illustrates the analyzer with the upper portion of the housing removed.

The manifold 210 mounts onto a circuit board 250, which has a connector 252 that connects with a ribbon cable 380 (FIG. 4). The manifold 210 includes a plate 212 and a manifold gas cap 214, which are ultrasonically welded together using known methods. The ultrasonic welding prevents gases from escaping the manifold 210. The plate 212 provides a platform for coupling other analyzer components, such as a pump 218 or solenoids 220. The gas cap 214 provides passages for gases to travel beneath the plate 212, so that the gases can travel to the various components.

The pump 218 is a positive displacement pump that helps to circulate the emission gases throughout the analyzer 100. Hoses 222 bring gases to and from the pump 218 for circulation. The pump 218 is secured on the manifold 210 by an assembly 224 (details in FIG. 6) so that it does not travel during operation.

Solenoids 220 are also mounted on the manifold 210 and help to direct the gases in the right direction toward the appropriate components, such as the pump 218. One solenoid is the zero solenoid, which helps to zero out the sensors (described below) before a sample of the emission gases are analyzed. The zero solenoid is connected to an outside source of ambient gas that will be used as the control gases. The other solenoid is the purge solenoid, which purges the contaminants and liquids from the filter 710. The solenoid directs the air from the pump to the filter 710 to force the contaminants and liquids from the filter. The solenoids' 220 are powered by power sources 234.

The manifold 210 can include a NOx sensor coupler 236 and an $O_2$ sensor coupler 238 mounted thereon. The couplers 236 and 238 can provide a threaded connection for their respective sensors. The NOx sensor 390 (FIG. 4) senses the presence and concentration of the NOx in the emission gases in parts per million (p.p.m.) and relays the data to a controller. Like the NOx sensor 390, the $O_2$ sensor 395 (FIG. 4) senses the presence and concentration of $O_2$ (p.p.m.) in the emission gases and relays the data to the controller.

A bench 300 (FIG. 3) which contains other sensors is not shown, but is placed on the circuit board 250 and secured by the bench assembly 240, which is mounted to the circuit board. The bench assembly 240 includes holders 242 located at the ends of the circuit board 250 and a clamp 246. The holder 242 supports the base 310 (FIG. 3) of the bench 300 and the clamp 246 clamps on a wall 320 (FIG. 3) of the bench.

Figure 3:
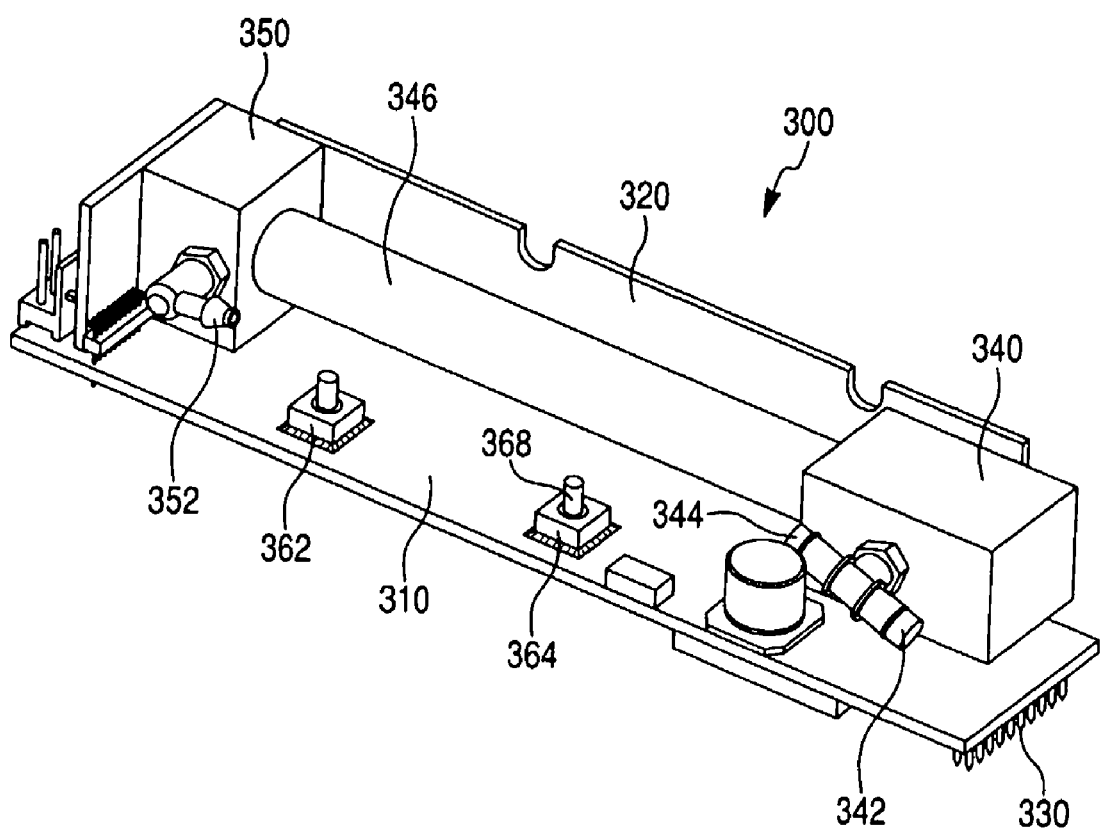
FIG. 3 illustrates a perspective view of an embodiment of a bench of the present invention.

FIG. 3 illustrates a perspective view of an embodiment of the bench 300 of the present invention. The bench 300 includes the base 310 and the wall 320 that mate with the holders 242 and clamp 246, respectively. An emitter 340 transmits non-disperse infrared (NDIR) along a tube 346 containing emission gases. The tube 346 can have an outer surface of brass and an inner surface plated with gold. Gold is preferable because it does not react with the emission gases. The emitter 340 can send the emission gases to the manifold 210 via connector 344. Additionally, the emitter 340 is in communication with an absolute pressure transducer 364 via a hose (not shown) that connects a connector 342 with the connector 368. The absolute pressure transducer 364 is a flow determiner to ensure that the tested gas flow is adequate for an accurate measurement. The type and concentration of the emission gases (such as CO, $CO_2$ and HC) can be measured by the absorbance of the NDIR's wavelength in the gases by a receiver 350. A zero reference is provided by a separate beam so that a chopper motor (that blocks the beam for a zero reference) is not required, thus making the analyzer 100 lighter. The emissions gases are exhausted from the receiver 350 via outlet 352 to continue its normal course.

The absolute transducer 364 and a differential transducer 362 are present on the base 310. The absolute pressure transducer 364 includes the connector 368 that can communicate with the emitter 340 via a hose. The differential transducer 362 provides altitude data for the analyzer 100 that can affect the reading. An interface 330 that can connect to the circuit board 250 through the ribbon cable 380 (FIG. 4) can relay data collected by the components of the bench 300.

FIG. 4 illustrates the analyzer 100 with the upper portion 120 of the housing 110 removed. The lower portion 130 contains the bench 300, the circuit board 250 and the manifold 210. Bench 300 is shown mated with the bench assembly 240 and the interface 330 is connected to the ribbon cable 380, which is connected to connector 253 on the circuit board 250. Also shown is the NOx sensor 390 and $O_2$ sensor 395 mounted on the manifold 210 at the NOx sensor coupler 236 and the $O_2$ sensor coupler 238, respectively.

Figure 5:
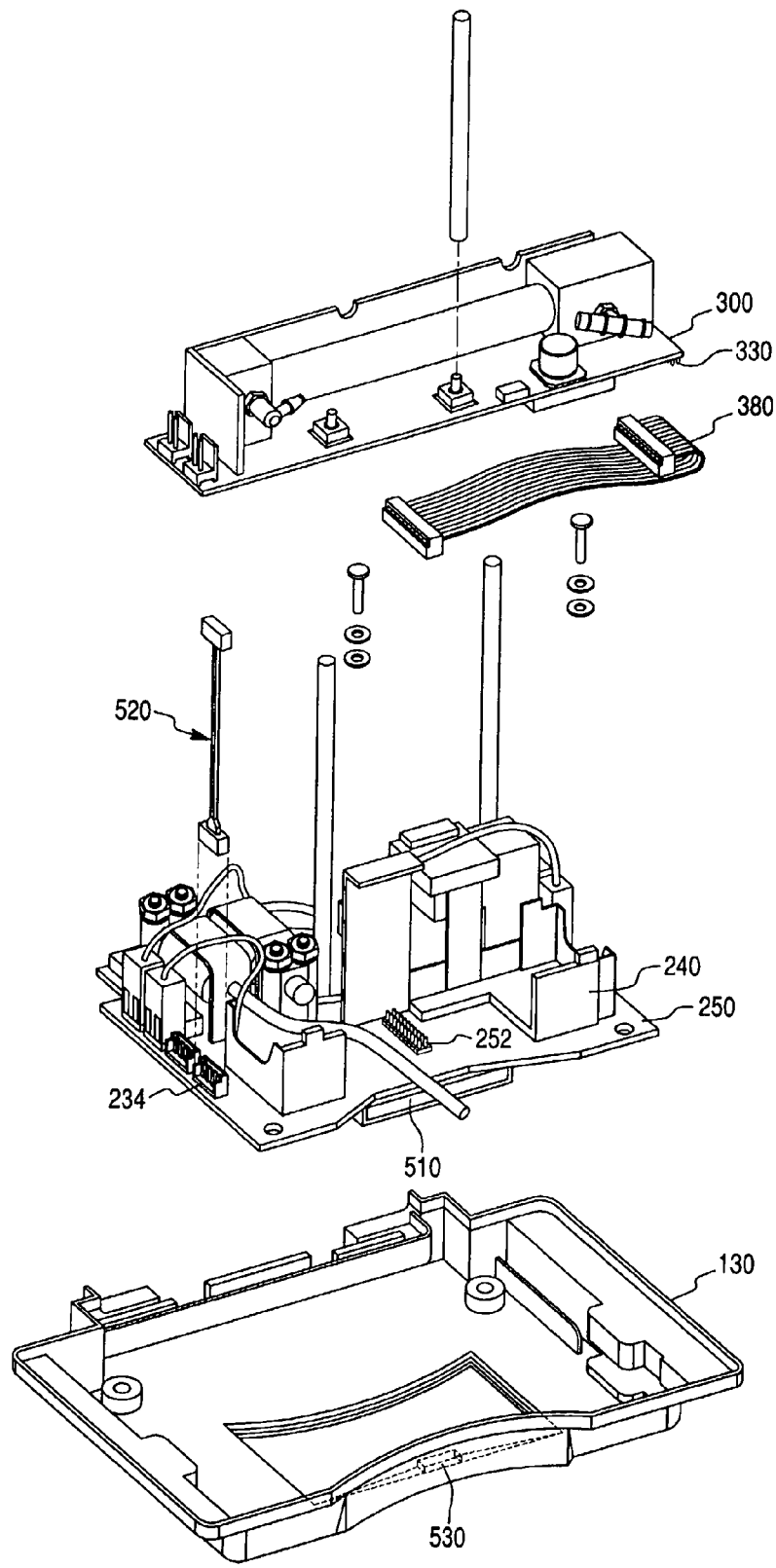
FIG. 5 is a blown-up view of the various components of the analyzer.

FIG. 5 is a blown-up view of the various components of the analyzer 100. The lower portion 130 of the housing 110 protects the lower components of the analyzer 100. A communication port window 530 that provides exterior access for a communication port 510 on the lower surface of the circuit board 250. The communication port 510 can communicate with an external device, such as a data processing device, a network device, a printer, a computer, a PDA (personal digital assistant) and other devices. The communication port 510 can transmit data via a direct connection to another device or can transmit data via a wireless means. FIG. 5 also illustrates the placement of the bench 300 on the bench assembly 240. The bench 300 is powered by power cable 520 that connects the bench with the power source 234. The ribbon cable 380 connects at one end to the interface 330 and at the other end to the connector 252 provides a communication means with the bench 300 and the circuit board 250.

Figure 6:
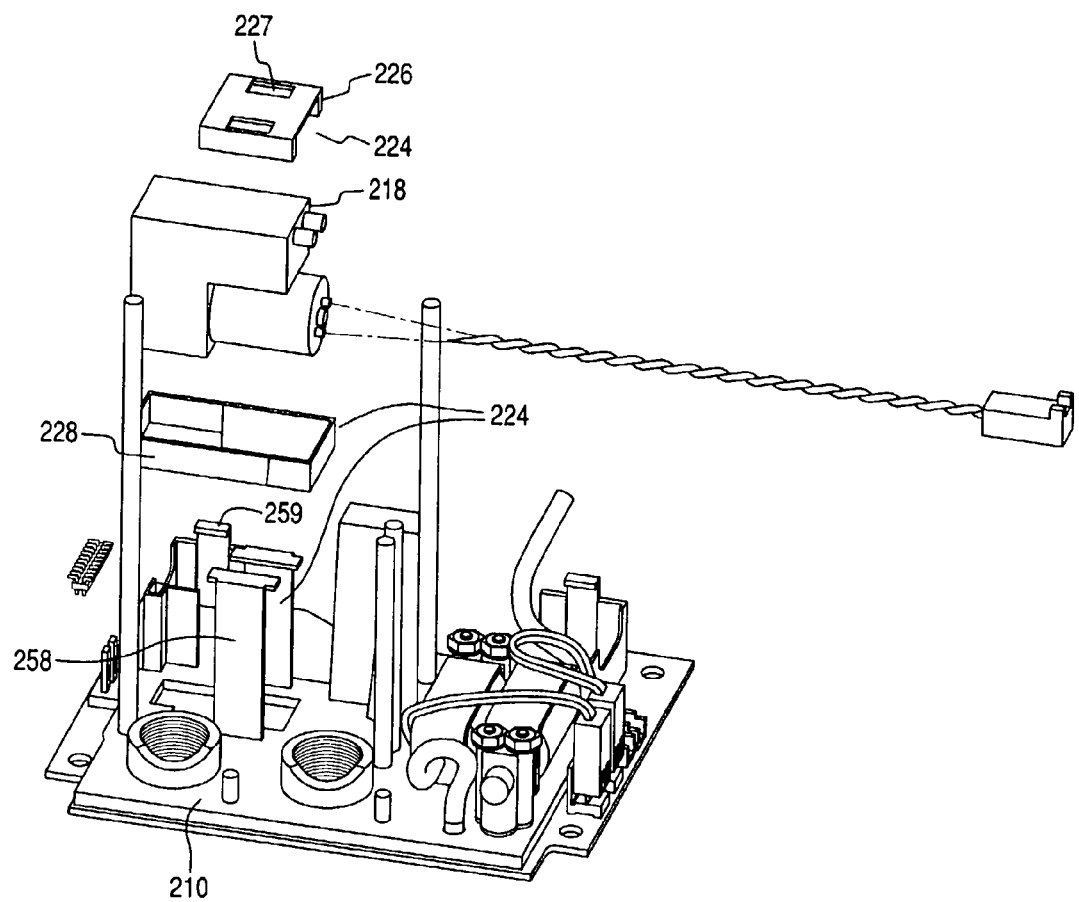
FIG. 6 is a blown-up view of an embodiment of a pump assembly of the invention.

FIG. 6 is a blown-up view of an embodiment of the pump assembly 218 of the invention. The assembly 224 secures the pump 218 to the manifold 210. The assembly 224 has an assembly base 228, an assembly cap 226 and retainers 258. The pump 218 is placed in the assembly base 228 to initially secure the pump. The assembly cap 226 has receiving slots 227 to receive the mating portion 259 of the retainers 258. The assembly cap 226 along with the retainers 258 prevent movement, such as side to side movement, of the pump 218 when it is in operation. In an embodiment of the invention, the assembly's 224 components, individually or in combination, can be made of an elastomeric material or other dampening materials. Some examples of elastomeric material include nitrile (NBR), butyl (IIR), styrene-butadiene (SBR), polyurethane (AU/EU), Silicone (PVMQ), polyisoprene (NR), and other elastomers. Conventional pumps are solidly mounted onto the chassis and are not made from an elastomeric material, thus the vibration made it difficult for the operator to hold the device for an extended period of time. Additionally, the pump can be noisy during its operation. Because of the properties of elastomeric material, the vibration is kept to a minimum and the noise from the pump 218 can be absorbed by the elastomeric assembly 224. Therefore, the analyzer 100 is more comfortable to use and can be held for a longer extended period of time, thus more tests can be conducted by the operator.

In an alternate embodiment, the individual or the combination of the assembly components (base, cap, retainers and other components) can be made from a semi-rigid or rigid material. Preferably the semi-rigid or rigid material can absorb the vibration and/or the noise of the pump.

Figure 7:
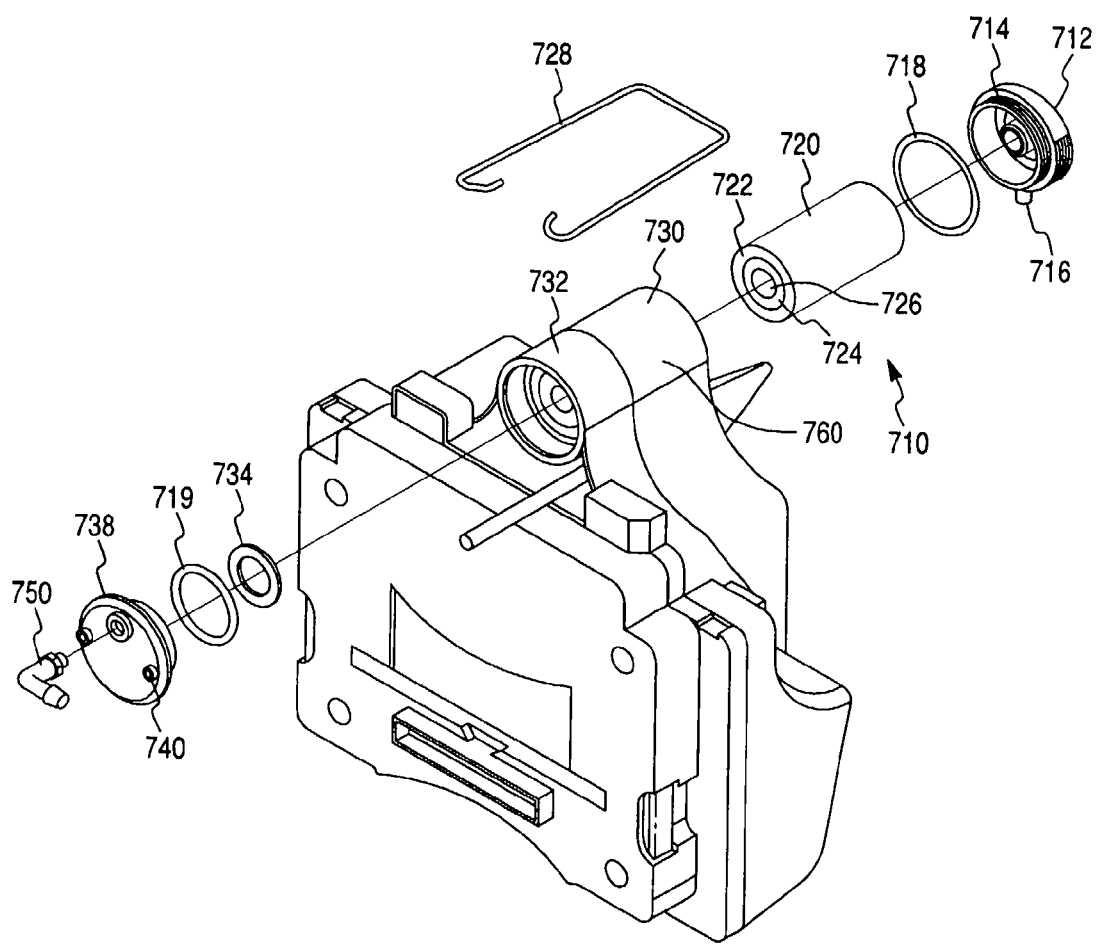
FIG. 7 is a blown-up illustration of the filter of an embodiment of the invention.

FIG. 7 is a blown-up illustration of the filter 710 of an embodiment of the invention. The filter 710 is a multi-stage filter having a filter cap 712, O-rings 718 and 719, primary filter element 720, filter retainer 728, filter holder 760, secondary filter element 734, filter base 738 and nozzle 750. The filter cap 712 having threads 714 secures the primary filter element 720 by being threaded into the filter holder 760. The filter cap 712 includes a filter connector 716 that can be hooked up to a hose that allows sample emission gases to enter of the analyzer from the exterior. O-ring 718 provides a seal between the filter cap 712 and the filter holder 760. The filter holder 760 includes an upper portion 730 and a lower portion 732 that can be threaded with the filter cap 712 and the filter base 738, respectively. The holder 760 and/or the filter cap 712 can be made of a clear material, such as polycarbonate (PC) so that the operator can view the accumulation of condensation and execute a purge function at the appropriate time. Additionally, the polycarbonate can also be used in other portions of the analyzer 100 because it is a high impact material and can provide protection of the analyzer and its components should the analyzer be dropped.

The emission gases is directed to the filter element 720 by the pump 218, where the gases pass through an outer filter element 722 where the larger particulate and "rough water" are removed. The sample emission gases can contain water or condensation as they travel in the hoses to the filter 710 due to temperature changes from the hot emission and ambient hoses. The emission gases then travel through the inner filter element 724 where additional filtering occurs to remove the smaller particulate and then to the annular area 726. The filtered emission gases then travel to the secondary filter element 734 where additional filtering can be accomplished. The O-ring 719 seals the filter base 738 to the lower portion 732 so that the emission gases do not escape. The filter base 738 has the nozzle 750 so that the filtered air can travel to the sensors for analysis. The filter base 738 also has a pair of retaining holes 740, which can provide a mating surface for an end of the filter retainer 728. The filter retainer 728 further retains the filter 710 to the analyzer 100.

The filter 710 is constructed and designed to reduce contamination and condensation and provides for a more accurate reading of the samples. Conventional filters require that the emission gases travel from the outside to one filter via a hose then to another filter by another hose and then to another filter via still another hose. As the emission gases travel in the hoses, it can get contaminated because of cracking and aging hoses and/or condensation can occur due to the many hoses that the gases must travel through to get to the filter. By having a multi-stage filter, where the filters are close to each other and no additional hoses are required between the filters, then chances of contamination and condensation are reduced. Additionally, the life of the filter can last longer because the filter is encased and sealed in the filter holder 760 and it does not have to filter out other external elements that can get into the filter other than from the sample hose.

The filter connector 716 is also used to purge the water from the filter holder 760. Over time, condensation will build up in the filter holder 760 and needs to be purged so that accurate readings of the emission gases can be taken. The operator can actuate the pump 218 to purge the liquid from the filter holder 760 and out the filter connector 716. However, for optimal purging, the filter connector should be in a certain orientation, preferably in the general direction of gravity. Because the analyzer 100 is lightweight and portable, the operator can set it down in various orientations, and thus, the analyzer may not be in the preferred orientation for purging. If the operator believes he purged the water from the filter holder 760, then he will believe that the readings are accurate when they may not be.

Figure 8:
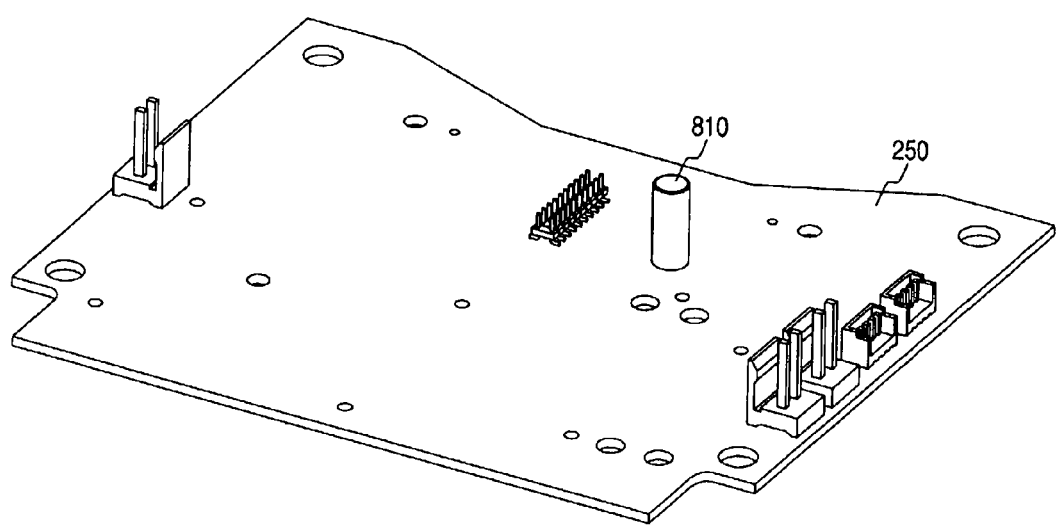
FIG. 8 illustrates an embodiment of an orientation device of the invention.

FIG. 8 illustrates an embodiment of an orientation device of the invention. In one embodiment of the invention, a tilt switch and/or accelerometer are used to notify the operator if the analyzer's 100 current orientation is preventing a satisfactory purging of the water. Conventional tilt switch can be used, such as a tilt switch 810 that is positioned on the circuit board 250. The tilt switch 810 can contain mercury, which can move based on the orientation of the tilt switch, and can detect changes in movement around them. The tilt switch can determine the orientation on all axis, such as X-axis, Y-axis, Z-axis, and any other axis. Additionally, accelerometer can also detect changes in the orientation of the analyzer 100. The accelerometer can be a one-axis, a two-axis, a three-axis accelerometer or as many axis type accelerometer, as desired. The tilt switch 810 and the accelerometer can communicate its data to the circuit board 250, which can act like a signal conditioner, and can relay to the orientation data to a controller on the bench 300. Although tilt switches and accelerometers can be used, other devices that can detect orientation of the analyzer 100 can be used, such as a GPS (Global Position System), or magnetic sensitive devices.

With the assistance of the tilt switch and/or accelerator, the analyzer 100 can notify the operator that it is not in the desired orientation for a purge, should the operator attempt to purge the water. The desired orientation can be preselected or predetermined so that purging only occurs when the analyzer is in the proper orientation. Thus, the operator can be assured that the purge went as expected and can rely on the readings from the analyzer 100. Additionally, if the purge function is automatic (discussed below) such as based on a certain time, in a certain amount of water or automatically as part of another operation, or other operations, and if the analyzer is not in the preferred orientation, the operator can be alerted or the purge function may not be performed. By alerting the operator of the incorrect orientation, the operator can reorient the analyzer 100 to the desired purging orientation. The operator is alerted visually, audibly, and tactically. A display or remote means, which can include an integrated display or a remotely located display. The remote means can communicate with the analyzer 100 via a wireless means or a connected means, such as Ethernet (wired and wireless).

The purging of the water from the analyzer 100 and the zero out can be done automatically, manually, or combined with other functions. Before a live reading of the emission gases is taken, the ambient air is taken into the analyzer so that the sensors can be zero out or the sensors can reset to take new readings. Additionally, the purge function can also be performed after the zero out. The purge function can also be performed before the zero out function. The order is not important. In an embodiment, the purge function and/or the zero function can be automatic, such as after startup, after the analysis is completed, after a certain amount of time has passed while the analyzer is on, after a number of samples have been taken, other time period or events.

In one embodiment of the invention, preferably when the operator activates the live reading mode of the analyzer 100, the analyzer can automatically purge, and then zero out. Alternatively, when the live reading mode is activated, the analyzer can automatically zero out then purge. In another embodiment, when the live reading mode is activated, the analyzer 100 can automatically and simultaneously purge and zero out. By having the purge and/or zero functions done automatically, the operator can concentrate on the analysis and does not have to remember when to purge and/or zero out.

Figure 9:
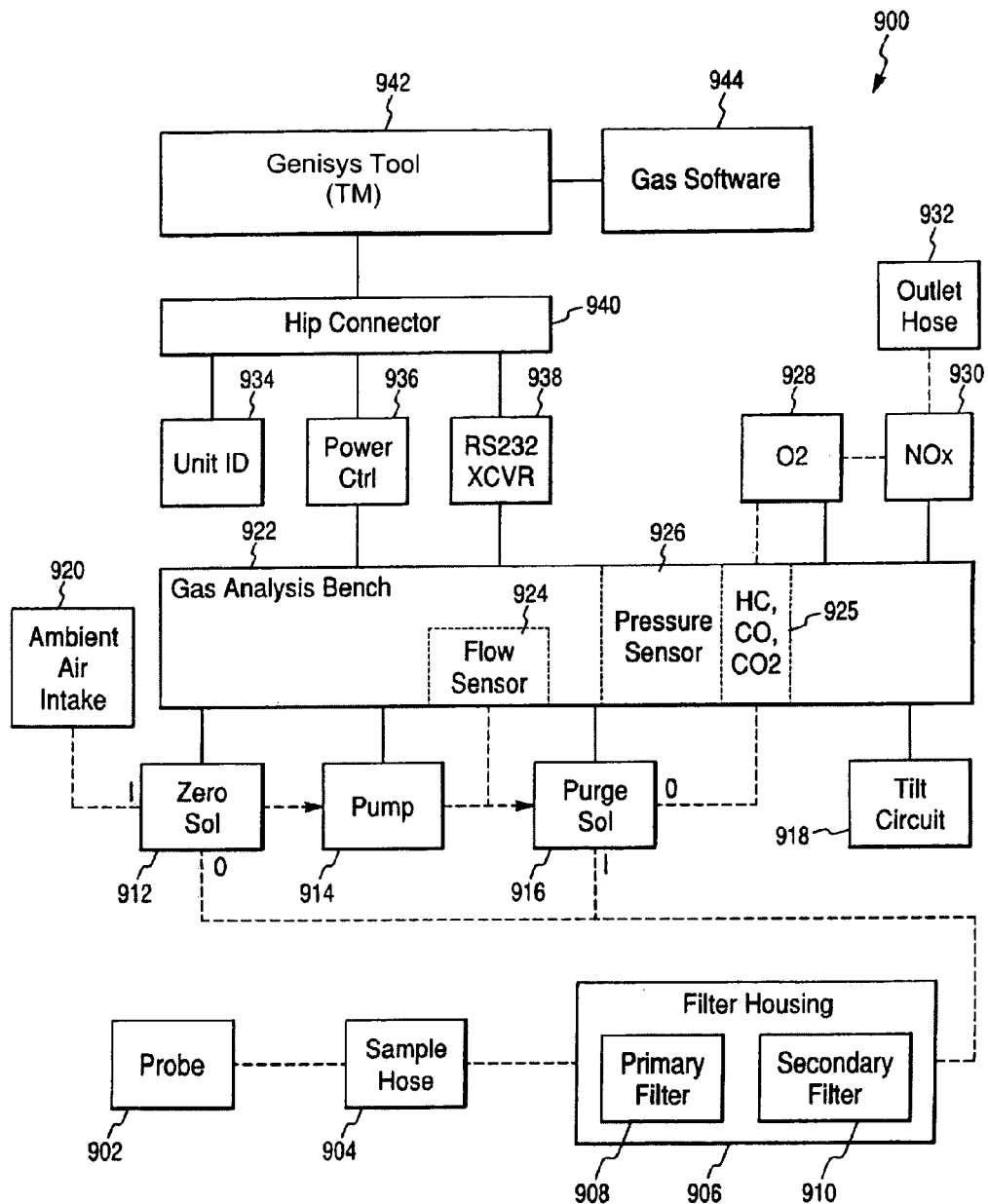
FIG. 9 is a block diagram of an embodiment of an analyzing system of the present invention.

FIG. 9 is a block diagram of an embodiment of an analyzing system 900 of the present invention. The analyzing system 900 can include an analyzer and an optional diagnostic device, such as the Genisys™ 942 that contains a gas analyzing software 944. The analyzer of the analyzing system 900 can include the analyzer 100, whose basic operation is explained herein and below.

A probe 902 is inserted or located near an exhaust system of a vehicle (not shown) and collects emission gases, which travels down a sample hose 904 to a filter housing 906. The filter housing 906 includes a primary filter 908, which can have two additional filters (inner and outer filter), and a secondary filter 910. The primary filter 908 will remove most of the particulate and any condensation. The secondary filter 910 will remove the remaining particulate and condensation. After the emission gases are filtered, the gases can travel through a zero solenoid 912, which at this point is shown in the inactive position, to a pump 914. The zero solenoid 912, during the zero out function, will open the pathway from an ambient air intake 920 and shutoff the gas pathway from the filter housing 906. The ambient air allows a baseline for the sensors 925, 928 and 930 to reset to zero, so that a live reading function can occur and an accurate reading can be made.

The pump 914 circulates the emission gases throughout the analyzer. The emission gases are then pumped to a purge solenoid 916, which is allows the gases to travel to the gas analysis bench 922. The purge solenoid, when in the purging mode, can purge by closing the pathway to the bench 922 and open the pathway to the filter housing 906. The zero solenoid 912 will close the pathway from the filter housing 906 and open the pathway from the ambient air intake 920. The pump 914 will draw in air from the air intake 920 and pump air through the purge solenoid 916 and to the filter housing 906 and forces the water to purge out the sample hose (which can have the probe 902 removed or attached).

The purge function (whether automatic or manual) may not occur properly if the analyzer not in the desired purging orientation. A tilt circuit 918 is provided to determine the orientation of the analyzer. The tilt circuit 918 can include tilt switches and/or accelerometer or other orientation determining devices. The tilt circuit 918 will alert the operator if the analyzer is not in the desired orientation when a purge function is activated, so that the operator can make the appropriate corrections.

At the bench 922, with a NDIR 925, the emission gases ($CO_2$, CO and HC) can be analyzed. The bench 922 includes a flow sensor 924 to ensure that the gases are flowing adequately for an accurate reading and a pressure sensor 926 to determine the altitude of the device, which can effect the reading. After the bench 922, the gases are pumped to the $O_2$ and NOx sensors 928, 930, where the respective gas readings can occur. Afterwards, the gases can be exhausted via an outlet hose 932.

Additional components of the analyzer can include the unit ID 934 so that if the analyzer is coupled to another device, such as the Genisys™, the analyzer would be identified. A power connection 936 and communication port 938 is also provided to communication with other devices via a wire or wirelessly. A hip connector 940 can connect the analyzer with another device.

The many features and advantages of the invention are apparent from the detailed specification, and thus, it is intended by the appended claims to cover all such features and advantages of the invention which fall within the true spirits and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

The invention claimed is:

1. An analyzer, comprising:
a sensor configured to take readings of a sample of gas supplied from an inlet;
an orientation device configured to determine an orientation of the analyzer;
a controller configured to reset said sensor to a baseline; and
purge the analyzer including a filter portion of the analyzer of contaminants, wherein said controller is configured upon actuation to reset said sensor and purge said analyzer.

2. The apparatus of claim 1, wherein said sensor includes a $NO_x$ sensor.

3. The apparatus of claim 1, wherein said sensor includes a $O_2$ sensor.

4. The apparatus of claim 1, wherein said controller activates a pump and a solenoid to reset said sensor and to purge said analyzer.

5. The apparatus of claim 4, wherein said pump is configured to circulate a gas throughout said analyzer and said solenoid is configured to direct said gas throughout said analyzer.

6. The apparatus of claim 5, wherein said solenoid is a zero solenoid and configured to direct said gas toward said sensor to reset said sensor to said baseline.

7. The apparatus of claim 5, wherein said solenoid is a purge solenoid and configured to direct said gas toward said filter portion to purge said analyzer and said filter portion of said analyzer.

8. The apparatus of claim 1, wherein the filter is configured to filter particulate matter.

9. A method of operating an analyzer, comprising the steps of:
actuating a sensor function of the analyzer to take a reading of a sample of gas supplied by an inlet;
actuating a zero function of the analyzer to zero out the analyzer;
determining the orientation of the analyzer; and
actuating a purge function of the analyzer to purge contaminants from the analyzer including a filter portion of the analyzer, wherein actuating the sensor function actuates the zero function and the purge function.

10. The method of operating the analyzer of claim 9, wherein actuating the sensor function automatically actuates the zero function and the purge function.

11. The method of operating the analyzer of claim 9, wherein actuating the sensor function, automatically actuates the zero function followed by determining the orientation of the analyzer which is followed by the purge function.

12. The method of operating the analyzer of claim 9, wherein actuating the sensor function, automatically actuates the purge function followed by the zero function.

13. The method of operating the analyzer of claim 9, wherein actuating the sensor function actuates the zero function and the purge function simultaneously and automatically.

14. The method of claim 9, wherein the filter is configured to filter particulate matter.

15. A system for operating an analyzer, comprising:
means for taking live reading of a gas sample;
means for determining an orientation of the analyzer;
means for purging contaminants from the analyzer including a filter portion of the analyzer; and
means for zeroing a sensor of the analyzer, wherein the means for taking live reading, the means for determining the orientation, the means for purging and the means for zeroing are in communication with each other, and wherein said means for taking live reading is configured upon actuation to actuate the means for zeroing, the means for determining the orientation, and the means for purging.

16. The system for operating an analyzer of claim 15, wherein upon actuation of said means for taking live reading, the means for zeroing is automatically actuated.

17. The system for operating an analyzer of claim 15, wherein when said means for taking live reading is actuated, the means for zeroing and the means for purging are simultaneously actuated with each other.

18. The system for operating an analyzer of claim 15, wherein upon actuation of said means for taking live readings, the means for determining the orientation is automatically actuated.

19. The system for operating an analyzer of claim 15, wherein when the means for taking live reading is actuated, the means for purging and the means for zeroing are automatically actuated.

20. The system of claim 15, wherein the filter is a mechanical filter.

* * * * *

UNITED STATES PATENT AND TRADEMARK OFFICE
CERTIFICATE OF CORRECTION

PATENT NO. : 7,043,958 B2 Page 1 of 1
APPLICATION NO. : 10/321585
DATED : May 16, 2006
INVENTOR(S) : Phillip McGee et al.

It is certified that error appears in the above-identified patent and that said Letters Patent is hereby corrected as shown below:

Column 10
Claim 1, line 6, please replace "analyzer;" with -- analyzer; and--;

Claim 1, lines 7-12, please replace:
"a controller configured to reset said sensor to a baseline; and
purge the analyzer including a filter portion of the analyzer of contaminants, wherein said controller is configured upon actuation to reset said sensor and purge said analyzer." with:
--a controller configured to reset said sensor to a baseline and to purge the analyzer including a filter portion of the analyzer of contaminants, wherein said controller is configured upon actuation to reset said sensor and purge said analyzer.--

Signed and Sealed this

Eleventh Day of December, 2007

JON W. DUDAS
*Director of the United States Patent and Trademark Office*